(12) United States Patent
Perl et al.

(10) Patent No.: US 10,632,148 B2
(45) Date of Patent: Apr. 28, 2020

(54) GROWTH CONTROL OF ORAL AND SUPERFICIAL ORGANISMS USING GALLIUM COMPOUNDS

(71) Applicant: MOUNT SINAI SCHOOL OF MEDICINE, New York, NY (US)

(72) Inventors: Daniel P Perl, Bethesda, MD (US); Sharon Moalem, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 0 days.

(21) Appl. No.: 14/985,474

(22) Filed: Dec. 31, 2015

(65) Prior Publication Data
US 2016/0113962 A1    Apr. 28, 2016

Related U.S. Application Data

(60) Continuation of application No. 14/208,748, filed on Mar. 13, 2014, now abandoned, which is a division of application No. 11/589,915, filed on Oct. 31, 2006, now abandoned.

(60) Provisional application No. 60/731,875, filed on Nov. 1, 2005.

(51) Int. Cl.

| | |
|---|---|
| *A61P 31/02* | (2006.01) |
| *A61P 31/04* | (2006.01) |
| *A61K 33/24* | (2019.01) |
| *A23K 20/20* | (2016.01) |
| *A61K 8/19* | (2006.01) |
| *A61Q 11/00* | (2006.01) |
| *A61Q 11/02* | (2006.01) |
| *A61L 15/46* | (2006.01) |
| *A23L 3/358* | (2006.01) |
| *A61L 12/08* | (2006.01) |
| *A61L 2/18* | (2006.01) |
| *A61L 2/16* | (2006.01) |
| *A61K 8/24* | (2006.01) |
| *A61K 8/365* | (2006.01) |
| *A23L 33/16* | (2016.01) |
| *A01N 55/02* | (2006.01) |
| *A01N 59/16* | (2006.01) |
| *A61K 31/28* | (2006.01) |

(52) U.S. Cl.
CPC .............. *A61K 33/24* (2013.01); *A01N 55/02* (2013.01); *A01N 59/16* (2013.01); *A23K 20/20* (2016.05); *A23L 3/358* (2013.01); *A23L 33/16* (2016.08); *A61K 8/19* (2013.01); *A61K 8/24* (2013.01); *A61K 8/365* (2013.01); *A61K 31/28* (2013.01); *A61L 2/16* (2013.01); *A61L 2/18* (2013.01); *A61L 12/088* (2013.01); *A61L 15/46* (2013.01); *A61Q 11/00* (2013.01); *A61Q 11/02* (2013.01); *A23V 2002/00* (2013.01); *A61K 2800/58* (2013.01); *A61L 2300/102* (2013.01); *A61L 2300/404* (2013.01); *Y02A 50/473* (2018.01); *Y02A 50/483* (2018.01)

(58) Field of Classification Search
CPC ........... A61P 31/02; A61P 31/04; A61K 33/24
See application file for complete search history.

(56) References Cited

U.S. PATENT DOCUMENTS

| | | | |
|---|---|---|---|
| 4,388,321 | A | 6/1983 | Robach et al. |
| 5,229,418 | A | 7/1993 | Collington et al. |
| 5,258,376 | A | 11/1993 | Bernstein |
| 5,358,705 | A | 10/1994 | Boggs et al. |
| 5,556,645 | A | 9/1996 | Bockman et al. |
| 5,574,027 | A | 11/1996 | Bernstein |
| 5,641,519 | A | 6/1997 | Gerber et al. |
| 5,679,377 | A | 10/1997 | Bernstein et al. |
| 5,686,116 | A | 11/1997 | Bockman et al. |
| 5,747,482 | A | 5/1998 | Bernstein |
| 5,843,936 | A | 12/1998 | Bernstein |

(Continued)

FOREIGN PATENT DOCUMENTS

| | | |
|---|---|---|
| EP | 0109564 | 5/1984 |
| EP | 0109564 A1 | 5/1984 |

(Continued)

OTHER PUBLICATIONS

Bernstein (Pharmacological Reviews (1998); 50(4):665-682). (Year: 1998).*

(Continued)

*Primary Examiner* — Soren Harward
*Assistant Examiner* — Chris E Simmons
(74) *Attorney, Agent, or Firm* — JMB Davis Ben-David (57) ABSTRACT

The present invention provides methods for treating or preventing diseases and disorders caused by iron-dependent pathogenic microorganisms, such as bacteria, fungi, and parasites, by applying a gallium compound to an affected area. In particular, the present invention provides methods for treating or preventing dental caries, vaginal infections, skin infections, and so forth. Gallium compounds can be formulated as toothpaste, mouthwash, cream, ointment, gel, solution, eye drops, suppository, and the like. Furthermore, the invention provides methods for controlling microbial growth on environmental surfaces, including those of toothbrush, denture, dental retainer, contact lens, catheter, food stuff, and so forth. In addition, the present invention provides animal feeds which contain gallium compounds that promote the animal growth and prevent the animals from infections as well as protect consumers from post processing infections.

7 Claims, 1 Drawing Sheet

(56) References Cited

U.S. PATENT DOCUMENTS

| | | | |
|---|---|---|---|
| 5,883,088 | A | 3/1999 | Bernstein |
| 5,916,885 | A | 6/1999 | Bernstein |
| 5,968,922 | A | 10/1999 | Bernstein |
| 5,981,518 | A | 11/1999 | Bernstein |
| 5,997,912 | A | 12/1999 | Schlesinger et al. |
| 5,998,397 | A | 12/1999 | Bernstein |
| 6,004,951 | A | 12/1999 | Bernstein |
| 6,048,851 | A | 4/2000 | Bernstein |
| 6,066,628 | A | 5/2000 | Stojiljkovic et al. |
| 6,087,354 | A | 7/2000 | Bernstein |
| 6,203,822 | B1 | 3/2001 | Schlesinger et al. |
| 6,221,350 | B1 | 4/2001 | Brown et al. |
| 6,287,606 | B1 | 9/2001 | Bockman et al. |
| 6,297,242 | B1 | 10/2001 | Hiasta |
| 6,506,413 | B1 | 1/2003 | Ramaekers |
| 7,560,421 | B2 | 7/2009 | Nakada et al. |
| 2002/0068761 | A1 | 6/2002 | Bernstein et al. |
| 2003/0083308 | A1* | 5/2003 | Bernstein ............ A61K 31/202 514/45 |
| 2003/0095950 | A1 | 5/2003 | McKinney et al. |
| 2004/0038956 | A1 | 2/2004 | Nakada et al. |
| 2004/0082925 | A1 | 4/2004 | Patel et al. |
| 2004/0087015 | A1 | 5/2004 | Vournakis et al. |
| 2005/0100563 | A1 | 5/2005 | Hexamer |
| 2005/0220895 | A1 | 10/2005 | Bucalo et al. |
| 2006/0018945 | A1 | 1/2006 | Britigan et al. |
| 2007/0231406 | A1 | 10/2007 | Bucalo et al. |
| 2008/0241275 | A1 | 10/2008 | Perl et al. |

FOREIGN PATENT DOCUMENTS

| | | |
|---|---|---|
| GB | 654472 A | 6/1951 |
| JP | 2005-503924 | 6/1993 |
| JP | 2000-516219 T | 12/2000 |
| JP | 2003-510362 T | 3/2003 |
| JP | 2004-097805 A | 4/2004 |
| JP | 2007-538090 T | 12/2007 |
| WO | WO-91/10437 A1 | 7/1991 |
| WO | WO-98/04264 A1 | 2/1998 |
| WO | WO-98/30102 A1 | 7/1998 |
| WO | WO-01/24799 A1 | 4/2001 |
| WO | WO-03/053347 | 7/2003 |
| WO | WO-05/055723 A1 | 6/2005 |
| WO | WO 05/58331 A1 | 6/2005 |
| WO | WO-05/112891 A2 | 12/2005 |
| WO | WO-07/053581 | 5/2007 |
| WO | WO-08/036787 | 3/2008 |
| WO | WO-09/009171 | 1/2009 |

OTHER PUBLICATIONS

Hill et al. (Infect Immun. Sep. 1998; 66(9): 4123-4129). (Year: 1998).*
Menon et al. (J Nucl Med 19:44.-47,1978). (Year: 1978).*
Healthwise. Vancomycin-Resistant Enterococci (VRE). CS Mott Children's Hosp. Michigan Med.) (Jul. 30, 2018). (https://www.mottchildren.org/health-library/tp23381spec). (Year: 2018).*
Davies, "Understanding Biofilm Resistance to Antibacterial Agents", Nature Reviews: Drug Discovery, 2: 114-122; 2003.
Champomier-Verges, Marie-Christine et al. "Acquisition of iron by the non-siderophore-producing Pseudomonas fragi" Microbiology (1996) 142: 1191-1199.
Bernstein, Lawrence "Mechanisms of Therapeutic Activity of Gallium" Pharmacological Reviews (1998) 50(4): 665-682.
Arnaut Rollier, Isabelle et al. "Identities of the Pseudomonas spp. In flora from chilled chicken" International Journal of Food Microbiology (1999) 48: 87-96.
Emery, Thomas et al."Siderophore-Mediated Mechanism of Gallium Uptake Demonstrated in the Microorganism Ustilago sphaerogena" the Journal of Nuclear Medicine (1980) 21(10): 935-939.
Ogunnariwo, J.A. et al. "Evidence for non-siderophore-mediated acquisition of transferrin-bound iron by Pasteurella multocida" Microbial Pathogenesis (1991) 11:47-56.
Pulz, M. et al. "Comparison of a Shiga Toxin Enzyme-Linked Immunosorbent Assay and Two Types of PCR for Detection of Shiga Toxin-Producing Escherichia coli in Human Stool Specimens" J. Clin. Microbiol. (Oct. 2003) 41(10): 4671-4675.
Gerrish, R.S. et al. "PCR versus Hybridization for Detecting Virulence Genes of Enterohemorrhagic Escherichia coli" Emerg Infect Dis. (Aug. 2007) 13(8): 1253-1255.
Cleary, T.G. "The role of Shiga-toxin-producing Escherichia coli in hemorrhagic colitis and hemolytic uremic syndrome" Seminars in Pediatric Infectious Diseases (Oct. 2004) 15(4): 260-265.
Tarr, Phillip I. et al. "Shiga-toxin-producing Escherichia coli and haemolytic uraemic syndrome" the Lancet_(Mar. 2005) 365(9464):1073-86.
Oughton, Matthew T. et al. "Acute Infectual Diarrhea" In: Rakel & Bope: Conn's Current Therapy, Philadelphia: Sanders Elsevier (2008).
Lee, A. et al. "A standardized mouse model of Helicobacter pylori infection: Introducing the Sydney strain" Gastroenterology, vol. 112, Issue 4, Apr. 1997, pp. 1386-1397.
Collery, et al. "Gallium in Cancer Treatment" Critical Reviews of Oncology/Hematology (2002) 42:283-296.
Sellers, L.J. "Big Pharma Bails on Anti-Infectives Research" Pharmaceutical Executive; Dec. 2003, vol. 23 Issue 12, p. 22.
Keenan, J.I. et al. "The effect of Helicobacter pylori infection and dietary iron deficiency on host iron homeostasis: a study in mice" Helicobacter. Dec. 2004;9(6):643-50.
Knobloch J.K. et al. "Biofilm formation is not necessary for development of quinolone-resistant "persister" cells in an attached Staphylococcus epidermidis population" Int J Artif Organs. Sep. 2008;31(9):752-60.
Arias, Cesar A. et al. "Antibiotic-Resistant Bugs in the 21$^{st}$ Century—A Clinical Super-Challenge" N Engl J Med (2009) 360(5):439-443.
Boucher, Helen W. "Bad Bugs, No Drugs: No ESKAPE! An Update from the Infectious Diseases Society of America" IDSA Report on Development Pipeline, (2009) CID 48:1-12.
Foucault, Cedric and Brouqui, Philippe "How to fight antimicrobial resistance" FEMS Immunology & Medical Microbiology, vol. 49, Issue 2, pp. 173-183, Mar. 2007.
Kristian, S. A. "The ability of biofilm formation does not influence virulence of Staphylococcus aureus and host response in a mouse tissue cage infection model" Microbial Pathogenesis, vol. 36, Issue 5, May 2004, pp. 237-245.
Lynch A.S and Robertson G.T "Bacterial and fungal biofilm infections" Annu. Rev. Med. 2008; 59:415-28.
Metlay, J.P. et al. "Antimicrobial drug resistance, regulation, and research" Emerg Infect Dis. (Feb. 2006) 12(2): 183-190.
O'Neill, Eoghan et al. "Association between Methicillin Susceptibility and Biofilm Regulation in Staphylococcus aureus Isolates from Device-Related Infections" J Clin Microbiol. May 2007; 45(5): 1379-1388.
Ramadhan, A.A. and Hegedus, E. "Biofilm formation and esp gene carriage in enterococci" J Clin Pathol, 2005, 58:685-686.
Smith, Karen et al. "Comparison of biofilm-associated cell survival following in vitro exposure of ethicillin-resistant Staphylococcus aureus biofilms to the antibiotics clindamycin, daptomycin, linezolid, tigecycline and vancomycin" International Journal of Antimicrobial Agents, vol. 33, Issue 4, Apr. 2009, pp. 374-378.
Stewart, Philip S." Mechanisms of antibiotic resistance in bacterial biofilms" Int. J. Med. Microbiol. (2002) 292:107-113.
Hubbard, Julia A. M. et al. "Effects of iron-limitation of Escherichia coli on growth, the respiratory chains and gallium uptake" Archives of Microbiology, Oct. 1986, vol. 146, Issue 1, pp. 80-86.
Bajpai, K.K. et al."Anti-fungal activities of diorgano gallium, indium and thallium diethyldithiocarbamates" Indian Phitopathology (1976) 29: 335-337.
Abu-Dari, Kamar et al."Antimicrobial activity of thiohydroxamic acids and their metal complexes: II. The synthesis and antimicrobial activity of N-methylthioacetohydroxamic acid and its zinc, copper, iron and gallium complexes" Dirasat (Pure and Applied Sciences) 1993, 20B(2): 7-16.

(56) References Cited

OTHER PUBLICATIONS

Srivastava T.N. et al. "Anti-microbial activities of diaryl gallium, indium and thallium compounds" Indian J. Agric. Sci., (1973), 43: 88-93.

Al-Aoukaty, Ala et al. "Gallium toxicity and adaptation in Pseudomonas fluorescens" *FEMS Microbiol Lett.* (May 1, 1992) 71(3):265-72.

Gascoyne, D.J. et al. "Capacity of siderophore—producing alkalophilic bacteria to accumulate iron, gallium and aluminum" Applied Microbiology and Biotechnology (Oct. 1991) vol. 36, Issue 1, pp. 136-141.

Wagner, S. et al. "Bismuth subsalicylate in the treatment of H2 blocker resistant duodenal ulcers: role of Helicobacter pylori" Gut (1992) 33:179-183.

"Innovation or Stagnation—Challenge and Opportunity on the Critical Path to New Medical Products" FDA U.S. Department of Health and Human Services (Mar. 2004).

"Bad Bugs, No Drugs—As Antibiotic Discovery Stagnates . . . A Public Health Crisis Brews" Infectious Diseases Society of America (Jul. 2004).

Harrison, P.F. and Lederberg, J. "Antimicrobial Resistance:: Issues and Options" National Academies Press (1998).

Jarvis, Lisa M. "An Uphill Battle: With short lives and uncertain profits, antibiotics are a unique development challenge for drug companies" Chemical & Engineering News (Apr. 14, 2008) vol. 86, Issue 15, pp. 15-20.

Jarvis, Lisa M. "Imminent Threat: As gram-negative bacteria become resistant to current antibiotics, the search for new drugs accelerates" Chemical & Engineering News (Apr. 14, 2008) vol. 86, Issue 15, pp. 21-24.

Jarvis, Lisa M. "Communal Living: Scientists across academia and industry are making a concerted effort to understand and control bacteria that form biofilms" Chemical & Engineering News (Jun. 9, 2008) vol. 86 Issue 23, pp. 15-23.

"Ordering—Eby's Gallium Nitrate Mineral Water 14% Concentrate" http://web.archive.org/web/20041015084724/coldcure.com/html/galiumsales.html (version Oct. 12, 2004).

"Eby's Gallium Mineral Water 14% Concentrate" Bottle Label, from http://web.archive.org/web/20050521015839/coldcure.com/gif/galiumlabelconcentrate.gif (version Oct. 12, 2004).

Bernstein, L. "Mechanisms of Therapeutic Activity for Gallium" Pharmacological Reviews (Dec. 1, 1998) vol. 50, No. 4, pp. 665-682.

Eby, G. "Is Navicular Disease in Horses Curable using Gallium Nitrate? Yes, if treatment is started sufficiently early—with lameness controlled in serious cases" http://www.coldcure.com/html/nay.html (rev. Oct. 15, 2005) pp. 1-27.

Howard, D.H. "Acquisition, Transport, and Storage of Iron by Pathogenic Fungi" Clin Microbiol Rev. (Jul. 1999) 12(3): 394-404.

Olakanmi, O. et al. "Gallium Disrupts Iron Metabolism of Mycobacteria Residing within Human Macrophages" Infect Immun. Oct. 2000; 68(10): 5619-5627.

Weinberg, E.D. "The Lactobacillus Anomaly: Total Iron Abstinence" Perspectives in Biology and Medicine, vol. 40, No. 4 (1997) pp. 578-583.

Litwin, C.M. et al. "Role of Iron in Regulation of Virulence Genes" Clinical Microbiology Reviews (Apr. 1993) 6(2):137-149.

Spatafora, G. et al. "Expression of *Streptococcus mutans* fimA is iron-responsive and regulated by a DtxR homologue" Microbiology (2001), 147:1599-1610.

Richardson, D.R. "Cytotoxic Analogs of the Iron(III) Chelator Pyridoxal Isonicotinoyl Hydrazone: Effects of Complexation with Copper(II), Gallium(III), and Iron(III) on Their Antiproliferative Activities" Antimicrobial Agents and Chemotherapy (Sep. 1997) 41(9): 2061-2063.

Feathrstone, J.D.B. " the Science and Practice of Caries Prevention" JADA, 131: 887-899 (Jul. 2000).

Evans, S.L. "Ferrous Iron Transport in *Streptococcus mutans*" Journal of Bacteriology (Dec. 1986) 168(3):1096-1099.

Heymann, P. et al. "The siderophore iron transporter of Candida albicans (Sit1p/Arn1p) mediates uptake of ferrichrome-type siderophores and is required for epithelial invasion" Infect Immun. (Sep. 2002) 70(9):5246-55.

Archibald, F. "*Lactobacillus plantarum,* an organism not requiring iron" FEMS Microbiology Letters, vol. 19, Issue 1, pp. 29-32 (Jun. 1983).

Adamson, R.H. et al. "Studies on the antitumor activity of gallium nitrate (NSC-15200) and other group IIIa metal salts" Cancer Chemotherapy Reports. Part 1 (1975) 59(3):599-610.

Foster, B.G. et al. "Gallium nitrate: the second metal with clinical activity" Cancer Treat Rep. (Nov. 1986) 70(10:1311-9.

Chitambar, C.R. et al. "Evaluation of Continuous-Infusion Gallium Nitrate and Hydroxyurea in Combination for the Treatment of Refractory Non-Hodgkin's Lymphoma" American Journal of Clinical Oncology (Apr. 1997) vol. 20, Issue 2, pp. 173-178.

Warrell, R.P. Jr. et al. "Gallium in the treatment of hypercalcemia and bone metastasis" *Important Adv Oncol.* (1989) pp. 205-220.

Brockman, R.S. et al. "Treatment of patients with advanced Paget's disease of bone with two cycles of gallium nitrate" Semin Arthritis Rheum. (Feb. 1994) 23(4):268-9.

Warrel, R.P. "Gallium nitrate inhibits calcium resorption from bone and is effective treatment for cancer-related hypercalcemia" J Clin Invest. (May 1984) 73(5): 1487-1490.

Matkovic, V. et al. "Gallium prevents adjuvant arthritis in rats and interferes with macrophage/T-cell function in the immune response" Curr Ther Res. (Aug. 1991) 50(2): 255-267.

Whitacre, C. et al. "Suppression Of experimental autoimmune encephalomyelitis by gallium nitrate" Journal of Neuroimmunology (1992)39: 175-182.

Orosz, C.G. et al. "Prevention of murine cardiac allograft rejection with gallium nitrate: Comparison with Anti-CD4 Monoclonal Antibodyl" Transplantation (Mar. 15, 1996) vol. 61, Issue 5, pp. 783-791.

Lobanoff, M.C. et al. "Effect of gallium nitrate on experimental autoimmune uveitis" Exp Eye Res. (1997) 65:797-801.

Levaditi, C. et al. "Le gallium, propriétés thérapetitiques dans la syphilis et les trypanosomiases expérimentales" C R Hebd Seances Acad Sci Ser D Sci Nat (May 1931) 192:1142-1143.

Olakanmi, O. et al. "Gallium inhibits growth of pathogenic mycobacteria in human macrophages by disruption of bacterial iron metabolism: a new therapy for tuberculosis and mycobacterium avium Complex?" Journal of Investigative Medicine (Apr. 1997) 3:234A.

Byers, B.R. et al. "Microbial Iron Transport: Iron Acquisition by Pathogenic Microorganisms" Metal Ions in Biological Systems (1973) 35:37-66.

Guerinot, M.L. "Microbial Iron Transport" Annual Review of Microbiology (1994) vol. 48: 743-772.

Shannon, R.D. "Revised effective ionic-radii and systematic studies of interatomic distances in halides and chalcogenides" Acta Cryst. (1976) A32: 751-767.

Huheey, James E. et al. "Inorganic Chemistry : Principles of Structure and Reactivity" 1993, 4th Edition, Harper Collins College Publishers.

Hancock, R.D. "Parametric correlation of formation constants in aqueous solution. 2. Ligands with large donor atoms" Inorg. Chem., 1980, 19 (9), pp. 2709-2714.

Clausen, J. "Ga binding to human serum proteins and tumor components" Cancer Res. (1974) 34:1931-1937.

Vallabhajosula, S. "Radiogallium localization in tumors: blood binding and transport and the role of transferrin" *J Nucl Med.* Jul. 1980;21(7):650--656.

Posey, J.E. et al. "Lack of a Role for Iron in the Lyme Disease Pathogen" Science (Jun. 2, 2000) vol. 288 No. 5471 pp. 1651-1653.

Weinberg, E.D. "Iron and Infection" Microbiol Rev. (Mar. 1978) 42(1): 45-66.

Neilands, J.B. "Evolution of biological iron binding centers" Structure and Bonding (1972) vol. 11, pp. 145-170.

Spiro, T.G. "The Hydrolytic Polymerization of Iron(III)" J. Am. Chem. Soc., Jun. 1966, 88 (12), pp. 2721-2726.

Van Der Helm, D. et al. "Hydroxamates and polycarboxylates as iron transport agents (siderophores) in fungi" Metal Ions in Fungi (1994) 11:39-98.

(56) References Cited

OTHER PUBLICATIONS

Crosa, J.H. "Signal Transduction and Transcriptional and Post-transcriptional Control of Iron-Regulated Genes in Bacteria" Microbiology and Molecular Biology Reviews, Sep. 1997, vol. 61, No. 3, pp. 319-336.

Payne, S.M. "Detection, isolation, and characterization of siderophores" *Methods Enzymol.* (1994) 235:329-44.

Chitambar, C.R. et al. "Uptake of Gallium-67 by Human Leukemic Cells: Demonstration of Transferrin Receptor-dependent And Transferrin-independent Mechanisms" Cancer Res. (Aug. 1, 1987) 47:3939-3934.

Todd. P.A. et al. "Gallium Nitrate: a Review of its Pharmacological Properties and Therapeutic Potential in Cancer-Related Hypercalcaemia" Drugs, Aug. 1991, vol. 42, Issue 2, pp. 261-273.

Jonkhoff, A.R. et al. "Gallium-67 radiotoxicity in human U937 lymphoma cells" Br J Cancer (Apr. 1993) 67(4):693-700.

Winn, D.M. et al. "Coronal and root caries in the dentition of adults in the United States, 1988-91" J Dent Res. (1996) 75(Spec Issue):642-6.

Stojilkovic, et al. "Non-iron metalloporphyrins: Potent antimicrobial compounds that exploit haem/Hb uptake systems of pathogenic bacteria" Mol. Micro. 31:429-442, 1999.

Eby, G. "Elimination of Arthritis Pain and Inflammation for over 2 years with a single 90 min topical 14% gallium nitrate treatment. Case reports and review of actions with gallium III", Medical Hypoth.65:1136-1141, 2005.

Jacobsen et al. J. Antimicrob Chem, 55:735-741, 2005.

Kohinke et al., "Treatment of Vancomycin-Resistant Enterococci: Focus on Daptomycin," Curr Infect Dis Rep (2017) 19: 33.

Russell et al., "Discovery of 4,6-bis(2-((E)-benzylidene)hydrazinyl) pyrimidin-2-Amine with Antibiotic Activity," ChemistryOpen (2019) 8: 896-907.

Wu et al., "In vitro activity of oritavancin alone or in combination against vancomycin-susceptible and -resistant enterococci," J Antimicrob Chemother, Feb. 8, 2019. doi: 10.1093/jac/dkz010.

\* cited by examiner

GROWTH CONTROL OF ORAL AND SUPERFICIAL ORGANISMS USING GALLIUM COMPOUNDS

CROSS REFERENCE TO RELATED APPLICATIONS

This is a continuation of co-pending U.S. patent application Ser. No. 14/208,748, filed Mar. 13, 2014 which is a divisional of U.S. patent application Ser. No. 11/589,915, filed Oct. 31, 2006, which claims the benefit of U.S. Provisional Patent Application No. 60/731,875, filed Nov. 1, 2005, the contents of all of which are incorporated herein by reference in their entirety.

FIELD

The present invention relates to methods of controlling growth of microorganisms, in particular, oral and superficial bacteria and fungi that cause disorders or diseases in host organisms, by applying gallium compounds to an affected or intended area topically or superficially. The invention further relates to formulations comprising gallium compounds for controlling growth of such microorganisms and objects or materials coated therewith or incorporating same. In addition, the invention relates to animal feeds containing gallium compounds.

BACKGROUND

Gallium is a group IIIa semi-metallic element that has been used for many years for diagnosing neoplasms and inflammation in the field of nuclear medicine. Gallium has also shown some efficacy in the treatment of cancers (Adamson et al., 1975, *Cancer Chemothe. Rept* 59:599-610; Foster et al., 1986, *Cancer Treat Rep* 70:1311-1319; Chitambar et al., 1997, *Am J Clin Oncol* 20:173-178), symptomatic cancer-related hypercalcemia (Warrell et al., 1989, in "Gallium in the treatment of hypercalcemia and bone metastasis", *Important Advances in Oncology*, pp. 205-220, J.B. Lippincott, Philadelphia; Bockman et al., 1994, *Semin Arthritis Rheum* 23:268-269), bone resorption (Warrell et al., 1984, *J Clin Invest* 73:1487-1490; Warrell et al., 1989, supra), autoimmune diseases and allograft rejection (Matkovic et al., 1991, *Curr Ther Res* 50:255-267: Whitacre et al., 1992, *J Newuro immunol* 39:175-182: Orosz C. G. et al., 1996, *Transplantation* 61:783-791: Lobanoff M. C. et al., 1997, *Exp Eye Res* 65:797-801), stimulating wound healing and tissue repair (Bockman et al., U.S. Pat. No. 5,556,645; Bockman et al., U.S. Pat. No. 6,287,606) and certain infections, such as syphilis (Levaditi C. et al., 1931, *C R Hebd Seances Acad Sci Ser D Sci Nat* 192:1142-1143), intracellular bacterial infections, such as tuberculosis, histoplasmosis, and leishmaniasis (Olakanmi et al., 1997, *J. Invest. Med.* 45:234A: Schlesinger et al., U.S. Pat. No. 6,203,822; Bernstein, et al., International Patent Application Publication No. WO 03/053347), *Pseudomonas aeruginosa* infection (Schlesinger et al., U.S. Pat. No. 6,203,822), and trypanosomiasis (Levaditi C. et al. supra).

Although the exact mechanism of gallium's activity against bone resorption and hypercarcemia is not well known, its antiproliferative properties against cancer cells and antimicrobial activities are said to be likely due to its competition with ferric iron (i.e., $Fe^{3+}$) for uptake by cancer cells or microorganisms (Bernstein, 1998, *Pharmacol Reviews* 50(4):665-682). Iron is an essential element for most living organisms, including many pathogens, and is required for DNA synthesis and various oxidation-reduction reactions (Byers et al., 1998, *Metal Ions Bio syst* 35:37-66; Guerinot et al., 1994, *Annu Rev Microbiol* 48:743-772; Howard, 1999, *Clin Micobiol Reviews* 12(3):394-404). $Ga^{3+}$ is known to have solution- and coordination-chemistries similar to those of $Fe^{3+}$ (Shannon, 1976, *Acta Crystallographica A*32:751-767; Huheey et al., 1993, In *Inorganic Chemistry: Principles of Structure and Reactivity I*, ed. 4, Harper Collins, NY: Hancock et al., 1980, In *Org Chem* 19:2709-2714) and behaves very similarly to $Fe^{3+}$ in vivo by binding to the iron-transport protein transferrin (Clausen et al., 1974, *Cancer Res* 34:1931-1937: Vallabhajosula et al., 1980, *J Nucl Med* 21:650-656). It is speculated that gallium enters microorganisms via their iron transport mechanisms and interferes with their DNA and protein synthesis.

U.S. Pat. No. 6,203,822 and International Patent Application No. WO 03/053347 disclose methods for treating patients infected with intracellular bacteria, in particular, species of the genus *Mycobacterium*, by intravenously or orally administering gallium compounds to patients infected by this class of bacteria (also see Olakanmi et al., 2000, *Infection and Immunity* 68(10):5619-5627). These organisms primarily infect macrophages, which are known to store large amounts of iron and overexpress transferrin receptors. Parenterally or orally administered gallium compounds are easily taken up by the macrophages through transferrin receptors and then, within the cells, are taken up by the infecting organisms, thereby interfering with the organisms' metabolism. The antimicrobial activities of gallium against microorganisms other than intracellular organisms have thus far not been explored to a great extent.

SUMMARY

This invention is based upon the inventors' use of gallium compounds to control the growth of pathogenic microorganisms at specific sites, such as oral cavities, nasal cavities, eyes, skins and vagina, in host organisms of such pathogens as well as on the surfaces of various objects that need to be kept free of such pathogens. Such a control is accomplished through the application of gallium compounds to an affected or intended area topically, or superficially.

Accordingly, the present invention provides methods for controlling the growth of iron-dependent pathogenic microorganisms, comprising applying gallium compounds to an affected or intended area topically, or superficially. In one aspect, the present invention provides methods for controlling growth of iron-dependent pathogenic microorganisms, such as bacteria and fungi, at specific sites in host organisms, preferably mammals, and most preferably humans, inflicted with such pathogens, by topically or locally applying gallium compounds to said sites. Those microorganisms include, but are not limited to, bacteria within the genera *Streptococcus, Staphylococcus, Yersinia, Salmonella, Chlamydia, Coxilla, Ehrlichia, Francisella, Legionella, Pasteurella, Brucella, Proteus, Hilicobacter, Klebsiella, Enterobacter, Escherichia, Tropheryma, Acinetobacter, Aeromonas, Alcaligenes, Campylobacter, Capnocytophaga, Bacillus, Clostridium, Corynebacterium, Erysipelothrix, Listeria, Mycobacterium, Pseudomonas*, and the like; and fungi, such as *Candida albicans, Microsporum canis, Sporothrix schenckii, Trichophyton rubrum, Trichophyton mentagrophytes, Malassezia furfur, Pityriasis versicolor, Exophiala werneckii, Trichosporon beigelii, Coccidioides immitis, Histoplama capsulatum, Blastomyces dermatitidis,*

*Aspergillus fumigatus, Epidermophyton* spp., *Fusarium* spp., *Zygomyces* spp., *Rhizopus* spp. *Mucor* spp., and so forth.

In a preferred embodiment, the microorganisms targeted by the present invention include, but are not limited to, those commonly found in the oral cavity, especially those bacteria which cause dental caries, plaques, periodontal diseases, halitosis, gingivitis and other oral diseases and disorders. Examples of such microorganisms include, but not by way of limitation, *Streptococcus nutans, Streptococcus sanguis, Streptococcus gordonii, Atopobium parvulum, Porphyromonas gingivalis, Eubacterium sulci*, and so forth. In another preferred embodiment, the microorganisms targeted by the present invention are pathogenic organisms causing infections in nasal and vaginal cavities, as well as on the skin surfaces and include *Staphylococcus aureus, Streptococcus pneumoniae*, β-hemolytic streptococci, *Corynebacterium minutissimum, Candida albicans, Microsporum audouinii, Microsporum canis, Microsporum gypseum, Microsporum canis, Sporothrix schenckii, Trichophyton rubrum, Trichophyton mentagrophytes, Pityriasis versicolor, Exophiala werneckii, Trichosporon beigelii, Malassezia furfur, Fusarium* spp., *Aspergillus* spp., and the like.

Accordingly, one aspect of the present invention provides methods for treating or preventing diseases or disorders caused by oral bacteria or fungi in a subject, comprising applying gallium compounds to the oral cavity. In a specific embodiment, the disease or disorder includes dental caries, gingivitis, halitosis, oral thrush and the like. Further, the present invention provides methods for treating or preventing a superficial infection in a subject, comprising topically applying gallium compounds to the affected area. In a specific embodiment, the superficial infection includes skin infections, vaginal yeast infections, ocular infections, and the like.

In another aspect, the present invention provides methods for controlling the growth of iron-dependent pathogenic microorganisms on the surfaces of objects, such as tooth brushes, dentures, dental retainers, contact lenses, bandages, dressings, medical devices, etc., by applying gallium compounds to the surfaces of the objects to disinfect them or to prevent them from contamination with pathogenic microorganisms. In yet another aspect, the present invention provides methods for controlling the growth of iron-dependent pathogenic microorganisms in foods, including grains (e.g., corn, wheat, rice, barley, and the like), vegetables (e.g., lettuce, spinach, potatoes, and the like), animal products, (e.g., fish, eggs and meat, and the like), by directly applying gallium compounds to the same by soaking, washing and/or spraying.

In another aspect, the present invention provides methods for controlling the growth of iron-dependent pathogenic microorganisms by applying gallium compounds to host organisms in need thereof in combination with probiotic microorganisms. Such probiotic microorganisms include, but are not limited to, non-pathogenic species of the genera *Lactobacillus, Lactococcus, Bifidobacterium*, and so forth, whose growths are not affected by the presence of gallium.

The present invention further provides formulations comprising gallium compounds for controlling the growth of iron-dependent pathogenic microorganisms. In a specific embodiment, the gallium compounds are formulated as toothpaste, a mouthwash, or a gargle for the application to the oral cavity. In another specific embodiment, the gallium compounds are formulated as ointments, lotions, creams, gels, solutions, eye drops, aerosols, and so forth, for topical or local applications. In yet another specific embodiment, the gallium compounds are formulated as a coating to the surfaces of an object to disinfect the same and/or to treat the infections in a wearer of the object (e.g., contact lenses to treat ocular infections). In yet another preferred embodiment, the formulations of the present invention may contain probiotic microorganisms in addition to gallium compounds.

In yet another aspect, the present invention provides animal feeds comprising gallium compounds with or without probiotics

DEFINITIONS

The term "subject" refers to an animal, including a fowl (e.g., chickens, turkeys, and the like), and a mammal such as a non-primate (e.g., cows, pigs, horses, cats, dogs, rats, etc.) and a primate (e.g., monkey and human), most preferably a human.

The term "topically", as opposed to "systemically", as used herein refers to an application of the gallium compounds to a definite area of the body of a subject and is interchangeably used with the term "locally." The term topically may refer to an application of the gallium compounds directly to an external area of the body, such as skin and eye as well as oral cavity, nasal cavity and vagina. The term topically may also refer to an application of the gallium compounds directly to a definite area inside the body which is exposed to an outer environment, for example, by injury or during surgery.

The term "superficially" as used herein refers to an application of the gallium compounds to the surfaces of an inanimate or animate object. The term superficially may refer to an application of the gallium compounds to the surfaces of an inanimate or animate object by coating. Alternatively, the term superficially may refer to an application of the gallium compounds to the surfaces of an inanimate or animate object by soaking the object in a solution of the gallium compounds or adhering/bonding the gallium compounds to the surface of the object.

The term "prophylactically effective amount" as used herein refers to that amount of the gallium compounds sufficient to prevent a disease or disorder associated with pathogenic microorganisms at a given site. A prophylactically effective amount may refer to the amount of the gallium compounds sufficient to prevent or suppress the growth of pathogenic microorganisms or kill pathogenic microorganisms at a given site.

The term "therapeutically effective amount" as used herein refers to that amount of the gallium compounds sufficient to treat, manage or ameliorate a disease or disorder caused by pathogenic organisms at affected sites. A therapeutically effective amount may refer to the amount of the gallium compounds sufficient to reduce the number of pathogenic microorganisms, to suppress the growth of pathogenic microorganisms (i.e., stasis), or to kill pathogenic microorganisms at the affected sites. Further, a therapeutically effective amount of the gallium compounds means that the amount of the gallium compounds alone, or in combination with other therapies, that provides a therapeutic benefit in the treatment, management, or amelioration of a disease or disorder.

The term "effective amount" as used herein in one aspect refers to that amount of the gallium compounds sufficient to control the growth of pathogenic microorganisms on the surfaces of inanimate objects. The term may refer to that amount of the gallium compounds sufficient to reduce the number of pathogenic microorganisms, to suppress the growth of pathogenic microorganisms (i.e., stasis), or to kill pathogenic microorganisms (i.e., disinfect) on the surfaces of objects. The term may also refer to that amount of the gallium compounds sufficient to prevent pathogenic microorganisms from attaching themselves to or colonize onto the surfaces of the objects. The term "effective amount' as used herein in another aspect in relation to animal feeds refers to that amount of the gallium compounds sufficient to promote animal growth and prevent infections when fed to the animals.

The term "probiotics" as used herein refers to viable microorganisms which alter the microflora by implantation or colonization in or onto the host, thereby exerting beneficial health effects on the host. The beneficial health effects of probiotics may be exerted particularly successfully in the environment which is hostile to pathogenic organisms but favorable for probiotics so that the growth of the probiotics outweigh that of the pathogenic organisms. Some examples of probiotics are non-pathogenic species of genera *Lactobacillus, Lactococcus, Peptostreptococcus, Bifidobacterium*, and so forth.

DETAILED DESCRIPTION

Iron Transport and Gallium

Figure 1:
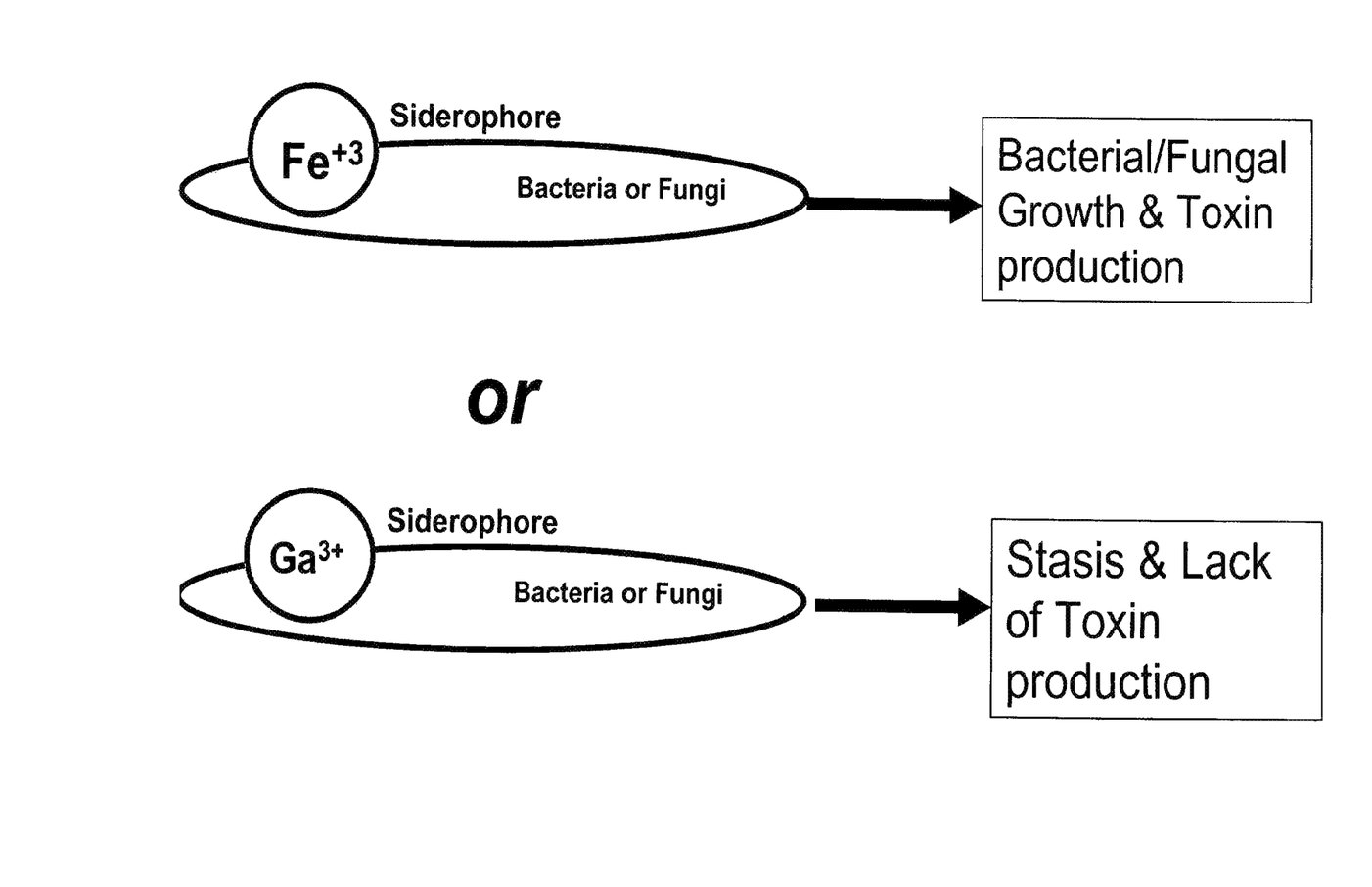
FIG. 1 is a diagram showing a mechanism by which microorganisms take in iron or gallium.

It is a well-known fact that most microorganisms, with a few exceptions (e.g., *Lactobacillus* spp.—see Archibald, 1983, *FEMS Microbiol Lett* 19:29-32; Weinberg, 1997, *Perspectives in Biology and Medicine* 40(4):578-583; and *Borrelia burgdorferi*—see Posey et al., 2000, *Science* 288: 1651-1653), require iron for their survival (Weinberg, 1978, *Microbiol Rev* 42:45-66: Neilands, 1972, *Struct Bond* 11:145-170). Despite the fact that iron is one of the most abundant metals, its availability to microorganisms is limited due to its existence as insoluble compounds (oxides-hydroxides) in aerobic environments (Guerinot, 1994, supra: Spiro, et al., 1966, *J Am Chem Soc* 88:2721-2725; Vander Helm et al., 1994, In *Metal ions in fungi* vol. 11, pp. 39-98, Marcel Dekker, Inc. New York, N.Y.). Accordingly, microorganisms, such as bacteria and fungi as well as parasites, have developed various mechanisms in order to acquire iron in the face of its limited availability in the environment (Howard, 1999, supra).

One such mechanism is the synthesis of potent iron-chelating compounds called siderophores. Microorganisms produce siderophores, which bind $Fe^{3+}$ in the environment and are transported into the cells via specific transport systems, where $Fe^{3+}$ is released as $Fe^{2+}$ and then stored. Known siderophores include hydroxamates, such as rhodotorulic acid, coprogens, ferrichromes, and fusarinines; polycarboxylates; phenolates-catecholates and desferioxamine (Howard, 1999, supra). Other mechanisms include direct internalization of iron complexed with siderophores or host iron transporters (e.g., transferrin and lactoferrin), membrane-associated reductase mechanisms, and receptor-mediated mechanisms as well as membrane-mediated direct-transfer mechanisms (Howard, 1999, supra; Crosa, 1997, *Microbiol Mol Biol Rev* 61:319-336; Payne, 1994, *Methods Enzymol* 235:329-344). The availability of iron through these mechanisms is closely linked to the virulence of microorganisms (Litwin et al., 1993, *Clin Microbiol Reviews* 6(2): 137-149), and each organism may have multiple alternative mechanisms for obtaining iron from iron-scarce environments to support its growth and survival (for example, see Spatafora et al., 2001, *Microbiology* 147:1599-1610).

It has been reported that gallium ion ($Ga^{3+}$) and ferric ion ($Fe^{3+}$) have strong biochemical similarities, in particular, with regard to their binding to proteins and chelators. These similarities are mainly attributed to their comparable ionic radii and the degrees of ionic (electrostatic) versus covalent contributions to bonding (for review, see Bernstein, 1998, supra). Because of these similarities, $Ga^{3+}$ can mimic $Fe^{3+}$ in various biological processes. For example, $Ga^{3+}$ binds to transferrin (see, for example, Clausen et al., 1974, *Cancer Res* 34:1931-1937; Vallabhajosula et al., 1980, *J Nucl Med* 21:650-656) and is transported into the cell via transferrin-mediated endocytosis (Chitambar, 1987, *Cancer Res* 47:3929-3934).

Without intending to be bound by theory, it is believed that $Ga^{3+}$ may competitively bind to siderophores and be easily taken up by microorganisms, where it can disrupt DNA and protein syntheses or bind to bacterial proteins and impair the growth of the microorganisms, thereby eventually leading to the stasis or death of the organisms. Alternatively, it is possible that $Ga^{3+}$ may occupy membrane-reductases of the microorganisms and prevent $Fe^{3+}$ from binding to the reductases to be reduced to $Fe^{2+}$ which would be more bioavailable than $Fe^{3+}$. Since the uptake of gallium does not immediately kill the microorganisms but rather leads to an initial stasis (i.e., a state where the growth or multiplication of microorganisms is inhibited), it has a reduced risk for generating resistant microorganisms.

The present invention takes advantage of these characteristics of gallium compounds and provides methods and formulations for controlling the growth of pathogenic microorganisms to treat or prevent infections caused by such pathogens.

Gallium Compounds

Gallium compounds suitable for use in the present invention include any gallium-containing compounds that are pharmaceutically acceptable and safe for mammalian use, in particular, for human use. Gallium compounds have been used diagnostically and therapeutically in humans and are known to be very safe for human use (see Foster et al., 1986, supra; Todd et al., 1991, *Drugs* 42:261-273; Johnkoff et al., 1993, *Br J Cancer* 67:693-700).

Pharmaceutically acceptable gallium compounds suitable for use in the present invention include, but not by way of limitation, gallium nitrate, gallium maltolate, gallium citrate, gallium phosphate, gallium chloride, gallium fluoride, gallium carbonate, gallium formate, gallium acetate, gallium sulfate, gallium tartrate, gallium oxalate, gallium oxide, and any other gallium compounds which can safely provide effective levels of element gallium in various applications. Furthermore, gallium complexes, such as gallium pyrones, gallium pyridones, and gallium oximes, as well as gallium bound to proteins, such as transferrin and lactoferrin, or gallium bound to siderophores, such as hydroxamates, polycarboxylates, and phenolates-catecholates, desferioxamine and other iron-chelators, such as cysteine, α-keto acids, hydroxy acids and pyridoxal isonicotinyl hydrazone class (Richardson et al., 1997, *Antimicrobial Agents and Chemotherapy* 41(9):2061-2063) and the like are also suitable for use in the present invention.

The therapeutically effective amount (i.e., dosage) of a gallium compound can vary based on the nature and severity of the disease or disorder to be treated, the location of the affected area, the age and immunological background of a subject, the types of gallium compound to be used, as well as other factors apparent to those skilled in the art. Typically, a therapeutically effective amount of a gallium compound can be that amount which gives gallium ion concentration, at the site of the application, of at least about 1 μM, at least about 50 μM, at least about 100 μM, at least about 500 μM, at least about 1 mM, at least about 10 mM, at least about 50 mM, at least about 100 mM, at least about 200 mM, up to about 500 mM. Due to gallium's low toxicity, the amount may be liberally increased to more than 500 mM but less than that amount which causes any toxicity. For reference, it has been reported that healthy adults can tolerate at least about 200 mg/m$^2$/day gallium nitrate intravenous infusion for at least 7 days (see Schlesinger et al., supra).

The prophylactically effective amount of a gallium compound may be that amount sufficient to prevent a disease or disorder associated with pathogenic microorganisms and may vary based on the location of the affected area, the types and the number of the pathogenic organisms in the area, the types of gallium compound to be used, as well as on the methods of application and other factors apparent to those skilled in the art. Typically, the prophylactically effective amount of a gallium compound may be that amount which gives gallium ion concentration, at the site of the application, of at least about 0.1 μM, at least about 50 μM, at least about 100 μM, at least about 500 μM, at least about 1 mM, at least about 10 mM, at least about 50 mM, at least about 100 mM, up to about 200 mM. Again, the amount of a gallium compound for prophylactic purposes may be liberally increased to more than 200 mM but less than the amount that causes any toxicity.

The effective amount of a gallium compound sufficient to control the growth of pathogenic microorganisms on the surfaces of inanimate objects may vary depending on the types of the objects, frequencies of their use, frequencies of their exposure to pathogenic organisms and other factors evident to those skilled in the art. Typically, the effective amount of a gallium compound for this application may be the amount which gives gallium ion concentration of at least about 50 mg/m$^2$, at least about 100 mg/m$^2$, at least about 200 mg/m$^2$, at least about 300 mg/m$^2$, at least about 500 mg/m$^2$, at least about 600 mg/m$^2$, at least about 700 mg/m$^2$, at least about 800 mg/m$^2$, at least about 900 mg/m$^2$, or at least about 1 g/m$^2$, on the surface area of the object.

Formulation of Gallium Compounds

The gallium compounds suitable for the present invention can be formulated in various forms depending on their applications. Accordingly, the present invention provides formulations comprising gallium compounds for controlling growth of iron-dependent pathogenic microorganisms. In a specific embodiment, the gallium compounds are formulated as toothpaste, a mouthwash, a gel or a gargle for the application to the oral cavity. In another specific embodiment, the gallium compounds are formulated as ointments, lotions, creams, gels, solutions, aerosols, suppositories and so forth, for topical or local applications. Any other formulations typically used for topical or local applications are applicable for the present invention.

In another preferred embodiment, the formulations of the present invention may further comprise probiotic microorganisms in addition to gallium compounds. When such formulations are applied to the affected area, probiotics can take over the microflora while the gallium compounds reduce or inhibit the growth of the pathogenic organisms, or kill the pathogenic organisms.

The gallium compound formulations of the present invention may further contain other active or inactive ingredients. For toothpaste, such other ingredients include, but are not limited to, potassium nitrate (to reduce tooth sensitivity), fluorides, abrasives, such as hydrated silica, surfactants, such as sodium lauryl sulfate, and ammonium lauryl sulfate, sequestering agents (to remove calcium and magnesium from saliva), such as tetrasodium pyrophosphate (TSPP), polymers, such as acrylic PVM/MA copolymer, polyethylene glycol (PEG), and polypropylene glycol (PPG), tooth whiteners, such as sodium carbonate peroxide, sweeteners, baking soda, as well as other anti-bacterial agents and fillers. For creams and lotions, such other ingredients include, but are not limited to, emollients, moisturizers, vitamins, antioxidants, surfactants, and so forth.

Dental Caries

The use of fluoride-containing products as well as the fluoridation of public water in the past 20 years have reduced the prevalence of dental caries in the U.S. (for review of this subject, see Featherstone, 2000, *JADA* 131:887-898). However, the recent report has shown that about 94% of all dentate adults, 18 years old or older, in the U.S. had evidence of treated or untreated coronal caries (Winn et al., 1996, *J Dent Res* 75:642-51), thus indicating that tooth decay still remains a major problem in adults as well as in children in the U.S.

Dental caries is a transmissible disease which is bacterially generated in combination with other pathological factors, such as reduced salivary function and frequency of use of fermentable carbohydrates (Featherstone, 2000, supra). Among resident oral bacteria, high levels of *Streptococcus mutans* and lactobacilli constitute the major etiological factors in caries formation. However, an antibacterial approach has not been the focus of regular oral hygiene measures taken in the U.S. to prevent or halt the progression of dental caries. An exception is a prescription of chlorhexidine gluconate rinse or gel for patients with high levels of bacteria: but it is difficult for clinicians to determine the levels of cariogenic bacteria in the mouth.

*Streptococcus mutans* (*S. mutans*) is also known to require iron uptake for its growth and survival and expresses several iron-responsive proteins (Spatafora et al., 2001, *Microbiology* 147:1599-1610). A fimA, one of the iron-responsive proteins, null mutation was not lethal in *S. mutans*, indicating that other mechanisms for iron uptake and transport are operating in this pathogenic organism (Spatafora et al., 2001, supra). It has been reported that *S. mutans* does not excrete a readily detectable phenolate or hydroxamate siderophores, but it has a membrane-reductase which reduces ferric ion to ferrous ion, which is subsequently transported into the cell by a membrane ferrous-translocating system (Evans et al., 1986, *J of Bacteriol* 168(3):1096-1099). Thus, iron uptake and transport seem to be crucial for cariogenic virulence of the organism.

Accordingly, the present invention provides a method for preventing dental caries, comprising applying a prophylactically effective amount of a gallium compound to a tooth surface and an oral cavity of a subject. In a preferred embodiment, the gallium compound is formulated as a toothpaste comprising a gallium compound and is applied to the tooth surface and oral cavity by brushing. In another preferred embodiment, the gallium compound is formulated as a mouthwash comprising a gallium compound and applied to the tooth surface by rinsing the oral cavity. In another preferred embodiment, the gallium compound may be formulated as an ointment or a gel to be applied to a tooth surface.

Vaginal Infections

Vaginal infections (or vaginitis) are among the most common medical concerns for women. Among vaginal infections, the most common is a yeast infection caused by the overgrowth of *Candida albicans* (*C. albicans*), which is a normal resident in the vagina in small numbers. It has been reported that siderophore uptake by sit (siderophore iron transport 1) gene product is required for *C. albicans* to invade and penetrate epithelial layers, indicating that iron uptake is directly linked to virulence factors of the organism (Heymann et al., 2002, *Infection and Immunity* 70(9):5246-5255). Thus, replacing iron with gallium compounds can effectively control the growth of *C. albicans* in the vagina. Accordingly, in a specific embodiment, the present invention provides a method for treating vaginal yeast infection comprising applying a gallium compound to the vagina of a subject. The gallium compound may be formulated as creams, ointments, gels, douches, or suppositories.

The present invention further provides a method for treating other types of vaginal infections, including, but not by way of limitation, bacterial vaginosis caused by pathogenic bacteria, such as *Gardnerella vaginalis, Bacteroides* spp., *Mobiluncus* spp., and *Mycoplasma hominis*, and parasitic vaginosis caused by *Trichomonas vaginalis*, by applying the gallium compounds in various formulations to the vagina.

Since most of the vaginal infections are the results of changes in the populations of the vaginal normal flora, populating the area with non-pathogenic normal residents, such as *Lactobacillus* spp., can also prevent the outgrowth of the pathogenic organisms. Accordingly, in a preferred embodiment, the present invention provides a method for treating vaginal infections, comprising applying a gallium compound in combination with a probiotic, such as *Lactobacillus acidophilus, Lactobacillus plantarum, Lactobacillus leichmannii, Lactobacillus johnsonni, Lactobacillus* and *delbrueckii*.

Disinfection of Inanimate or Animate Objects

Antimicrobial activities of the gallium compound can be also used for disinfecting or protecting the surfaces of inanimate or animate objects from microbial contaminations. Accordingly, the present invention provides a method for controlling a growth of microorganisms on a surface of an inanimate or animate object, comprising applying an effective amount of a gallium compound to a surface of the object.

For example, toothbrushes, dentures and dental retainers often harbor carried-over oral microorganisms and it is desirable to prevent the growth of such organisms on the surfaces of these products from oral hygiene viewpoints. Accordingly, in a specific embodiment, the present invention provides a method for disinfecting the objects, such as a toothbrush, a denture, a dental retainer, and other dental devices, by applying an effective amount of a gallium compound to a surface of the object. The gallium compounds may be applied to the surface of the object by dipping, brushing, spraying or coating. The coating may be based on a certain polymer that allows slow diffusion of the gallium compound at such a rate that it prevents microorganisms from growing on the surface of the object. Examples of polymer coatings include, but are not limited to, hydroxyapatite, polymethacrylates, tricalcium phosphate, polyanhydrides, hydrocarbon elastomers, methyl- and ethyl cellulose, hydroxypropyl cellulose, cellulose acetate, phthalate, and so forth. Alternatively, the gallium compounds can be incorporated into materials, for example, the polymers (e.g., thermoplastics, thermoset resins, and the like), metals, and the like, which form the object itself (e.g., bristles of a toothbrush, a catheter, medical equipment, injection needles, and the like).

In another specific embodiment, the present invention provides a method for disinfecting contact lenses by applying an effective amount of a gallium compound to a surface of the lenses. The lenses may be disinfected by dipping them in the gallium compound solution, or by coating their surfaces with or without a certain polymer containing the gallium compounds as described above.

In another specific embodiment, the present invention provides a method for disinfecting skin surfaces of a subject, comprising applying the gallium compounds to the same, for example, as soap, shampoo, skin disinfectant (e.g., hand), and the like. Preferably, the gallium compounds are applied to the skin surfaces in the form of cream, lotion, solution, aerosol, or ointment.

In another specific embodiment, the present invention provides a method for controlling the growth of microorganisms in drinks and foods, including grains, vegetables, animal products, such as fish, eggs, dairy products, meat, and the like, comprising applying the gallium compound directly to the same by washing, soaking and/or spraying. Such a treatment of foods can effectively protect the consumers from food poisoning.

The present invention also provides medical implants, bandages, wound dressings which are surface-coated with the gallium compounds.

Furthermore, the present invention provides a method for controlling a microbial growth on various environmental surfaces in households, hospitals, schools, etc., by applying the gallium compounds to the same. The gallium compounds can be used against any gallium-susceptible pathogenic microorganisms as discussed throughout the present specification (see Section 3 and Subsections 5.4 and 5.5, supra, and Subsections 5.7 and 5.8, infra), including the microorganisms that are known to have become resistant to first-line antibiotics. Such microorganisms include *Escherichia coli* O157 (a causative organism for gastroenteritis, haemorrhagic colitis or urinary and genital tract infections), vancomycin-resistant *Enterococcus faecalis* (a causative organism for endocarditis, urinary tract infections, and wound infections), methicillin-resistant *Staphylococcus aureus* (MRSA; a causative organism for various skin infections, eye infection, wound infections, and so forth), *Salmonella typhi* (the causative organism for typhoid fever), and the like. The applications of the gallium compounds to various surfaces are cost effective and significantly reduce microbial contaminations in the environment without increasing the development of antibiotic-resistant microorganisms.

Animal Feeds

The use of antibiotics in animal feeds to boost animal growth and prevent infections has caused in a major way the development of drug-resistant bacteria. Such a use of antibiotics in poultry and beef industries has resulted in the emergence of antibiotics-resistant pathogens among species of genera *Salmonella, Campylobacter, Shigella, Brucella*, and so forth. Thus, some countries are in the process of banning the use of antibiotics in animal feeds.

As discussed above, gallium compounds have less risks of generating drug-resistant pathogens than do regular antibiotics and, therefore, are viable alternatives to the conventional antibiotics. Accordingly, the present invention provides an animal feed comprising an effective amount of a gallium compound. The effective amount of a gallium compound in an animal feed sufficient to promote animal growth and prevent infections can be readily determined based on the therapeutic or prophylactic dosages of the gallium compounds described in the previous sections (see Subsection 5.2) and such a determination is within the ability of those skilled in the art.

In a preferred embodiment, the animal feed of the present invention may further comprise probiotics. The health benefits of probiotics are discussed in Subsections 3.1 and 5.3. Typical probiotic compositions and methods for increasing the number of probiotic or resident microorganisms in the gastrointestinal tract of an animal are disclosed, for example, in U.S. Pat. No. 6,221,350.

Miscellaneous Applications

Gallium compounds may be utilized in many different applications other than those described in the previous sections. For example, gallium compounds may be applied topically or directly to a body area, including an open wound and an internal organ or tissue exposed to an outer environment during surgery in addition to an external area, that needs to be protected from or is afflicted with various infections caused by pathogenic organisms. Such infections include, but not by way of limitation, skin infections, such as cellulites, folliculitis, boils, carbuncles, erysipelas, impetigo, erythrasma, paronychia, staphylococcal scalded skin syndrome, candidiasis (e.g., oral thrush), ring worm, tinea versicolor, etc. as well as eye infections, such as blepharitis, hordeola, conjunctivitis, etc., and nasal infections. Causative organisms for skin infections include, but are not limited to, species of *Staphylococcus*, such as *S. aureus* and *S. epidermidis*; Group A streptococci, such as *Streptococcus pyogenes*: *Pseudomonas aeruginosa*, and the like. Typical yeasts or fungi that cause skin infections include *Candida albicans*, species of genus *Microsporon*, such as *M. auduini* and *M. canis*; species of *Trichophyton*, such as *T. metagrophyte* and *T. tonsurans*, and the like. Causative organisms for eye infections include *Staphylococcus aureus*, *Streptococcus pyogenes*, *Haemophilus influenzae*, *Chlamydia trachomatis*, *Neisseria gonorrhoeae*, *Propionibacterium* spp., *Nocardia* spp., *Bacteroides* spp, *Fusarium* spp. and so forth. Nasal infections caused by *Streptococcus pneumoniae* may lead to ear infection, sinusitis, bronchitis, pneumonia, etc. The infections caused by these organisms have become more and more common because of the development of drug-resistant microorganisms, such as methicillin-resistant *Staphylococcus aureus* (MRSA), as well as the increased number of immunocompromised individuals due to HIV infection or AIDS, organ transplants, treatments for autoimmune diseases, and so forth. Thus, the applications of gallium compounds for human uses as well as veterinarian uses are very beneficial especially in view of their low toxicity and low risks for generating resistant microorganisms. Other applications in the fields of food industries, agricultural industries, fishing industries and so forth are also possible.

EXAMPLES

Susceptibility of Microorganisms to Gallium

Susceptibility of various microorganisms to gallium was tested by determining the minimum inhibitory concentration (MIC) and minimum bactericidal concentration (MBC) for each microorganism using gallium nitrate. In general, MIC is determined by (i) mixing a series of broths, each containing a standard number of microorganisms, with serially diluted solutions of the gallium compound; and (ii) determining the MIC, after incubation, that is the lowest concentration of the gallium compound that has inhibited the growth of the microorganism. The lower the MIC, the more susceptible the organism is. The MBC is determined by subculturing an aliquot of each sample from the MIC test on an appropriate agar plate containing no gallium compound. After incubation, the MBC is determined to be the lowest concentration of the gallium compound at which no growth is observed.

Specifically, in the present experiment, two grams of gallium nitrate powder were dissolved in 10 ml of filter-sterilized deionized water and the resulting 20% (w/v) (i.e., 200 mg/ml) solution was once again filter-sterilized. Two-fold serial dilutions were prepared in sterile deionized water down to 0.156% (i.e., 1.56 mg/ml) for the tests for the most organisms, except for the tests for *Candida albicans* and *Streptococcus mutans*, in which 10%, 1%, 0.5%, 0.1%, 0.05%, 0.01%, 0.005% and 0.001% of gallium nitrate solutions were prepared.

Table 1 shows the list of microorganisms tested for MIC and MBC. All organisms were obtained from the American Type Culture Collection (ATCC), Manassas, Va. Each microorganism was picked from the seed culture (see Table 1) and inoculated in an appropriate type of broth to obtain a 0.5 McFarland turbidity standard. The standard suspension of the microorganism was then diluted to 1:100 with the broth and used for the tests.

TABLE 1

| TEST ORGANISM | ATCC # | SEED CULTURE |
|---|---|---|
| *Candida albicans* | 10231 | On Sabouraud dextrose agar, at 25-30° C. for 24-48 hours. |
| *Streptococcus mutans* | 25175 | On blood agar, at 35-37° C. for 24-48 hours, with $CO_2$. |
| *Porphyromonas gingivalis* | 33277 | On *Brucella* blood agar, at 35-37° C. for 7 days under anaerobic conditions. |
| *Pseudomonas aeruginosa* | 15442 | On tryptic soy agar with 5% sheep blood (BAP), at 35-37° C. for 24-48 hours under aerobic conditions. |
| Methicillin-resistant *Staphylococcus aureus* (MRSA)[a] | 33592 | |
| Vancomycin-resistant *Enterococcus faecalis* (VRE)[b] | 51575 | |
| *Escherichia coli* O157: H7 | 35150 | |
| *Salmonella typhi* | 6539 | |
| *Campylobacter jejuni* | 29428 | On *Brucella* agar with 5% sheep blood, at 35-37° C. for 48 hours under microaerophilic conditions (CampyPak™ by BBL Microbiology Systems, Cockeysville, Md). |

[a]Antibiotics resistance of the organism was confirmed by CLSI (Clinical Laboratory Standards Institute) Oxacillin disk-diffusion test. The zone of inhibition was 6 mm (CLSI Oxacillin resistant range: ≤10 mm).
[b]Antibiotics resistance of the organism was confirmed by CLSI Vancomycin disk-diffusion test. The zone of inhibition was 10 mm (CLSI Vancomycin resistant range: ≤14 mm).

Each microorganism was tested in duplicate by either a microdilution broth method in 96-well plates (i.e., 0.1 ml of the gallium nitrate solution mixed with 0.1 ml of the microorganism suspension) or a macrodilution broth method in test tubes (i.e., 1 ml of the gallium nitrate solution mixed with 1 ml of the microorganism suspension) as follows:

Microdilution broth method: *Candida albicans*; *Streptococcus nutans*; *Escherichia coli* O157:H7; and *Campylobacter jejuni*.

Macrodilution broth method: Methicillin-resistant *Staphylococcus aureus* (MRSA); Vancomycin-resistant *Enterococcus faecalis* (VRE); *Salmonella typhi*; *Pseudomonas aeruginosa*; and *Porphyromonas gingivalis*.

The growth of the microorganisms were determined by visual observation of turbidity in the samples.

The following controls were incubated together with the test samples: Viability control: A mixture of equal volumes of deionized water and an appropriate broth inoculated with a test microorganism but without gallium nitrate; and Sterility control: A mixture of equal volumes of deionized water and an appropriate broth without either microorganisms or gallium nitrate.

Purity of each microorganism was confirmed by streaking an appropriately diluted suspension of the microorganism onto an appropriate agar plate to obtain isolated colonies and observing colony morphology.

The concentrations of microorganisms in the suspension used in MIC test were determined by inoculating serial dilutions of the suspensions onto appropriate agar plates and counting the number of colonies.

To determine MBC, 10 μl of each sample used in MIC were inoculated onto an appropriate agar plate and incubated. The lowest concentration of the gallium nitrate that showed no growth was determined to be the MBC.

The results are shown in Table 2 below.

TABLE 2

| Test Organism | Broth (MIC) | Agar Plate (MBC) | Incubation Condition | Final Concentration of Organism (CFU/ml) | MIC (mg/ml) | MBC (mg/ml) |
|---|---|---|---|---|---|---|
| Candida albicans | Sabouraud Dextrose | Sabouraud dextrose agar | At 27° C. for 48 hours | $9.75 \times 10^5$ | 10 | >100 |
| Streptococcus mutans | Brain Heart Infusion | Blood agar | At 36° C. For 48 hours | $4.1 \times 10^6$ | ND* | 5.0 |
| Porphyromonas gingivalis | Fluid Thioglycollate | Brucella blood agar | At 36° C. for 14 days(plate controls: for 5 days) | $7.2 \times 10^7$ | ND | <0.78 |
| Pseudomonas aeruginosa | Muller Hinton | Tryptic soy agar with 5% sheep blood | At 36° C. for 48 hours | $7.6 \times 10^5$ | ND | 6.25 |
| Staphylococcus aureus (MRSA) | Muller Hinton | Tryptic soy agar with 5% sheep blood | At 36° C. for 48 hours | $5.2 \times 10^5$ | ND | 12.5 |
| Enterococcus faecalis (VRE) | Muller Hinton | Tryptic soy agar with 5% sheep blood | At 36° C. for 48 hours | $3.9 \times 10^5$ | ND | 25 |
| Escherichia coli O157:H7 | Muller Hinton | Tryptic soy agar with 5% sheep blood | At 36° C. for 48 hours | $1.38 \times 10^6$ | ND | 6.25 |
| Salmonella typhi | Muller Hinton | Tryptic soy agar with 5% sheep blood | At 36° C. for 48 hours | $8.3 \times 10^5$ | ND | 6.25 |
| Campylobacter jejuni | Muller Hinton | Tryptic soy agar with 5% sheep blood | At 36° C. for 48 hours | $4.9 \times 10^5$ | ND | <0.78 |

*ND: Not determined due to non-specific turbidity caused by the precipitation of gallium nitrate at some dilutions.

The following examples are intended to illustrate, without limitation, preferred embodiments of the present invention as applied to practical modalities for the prevention and treatment of bacterial and fungal infections.

Example 1 Toothpaste Formulation

A toothpaste is formulated to contain gallium nitrate at 50 μM and 0.2% by weight sodium fluoride as active ingredients in the treatment and prevention of dental and periodontal disease. The formulation also contains conventional inactive ingredients including water, sorbitol, glycerin, hydrated silica, polyethyleneglycol, xanthan gum, sodium saccharin, methylparaben, and propylparaben. These are blended in amounts known to those skilled in the art to obtain a toothpaste of appropriate consistency. The formulation can be packaged in conventional toothpaste tubes, and used in the normal manner.

Example 2 Treatment of Vaginal Yeast Infection

The present invention is applied to the formulation of suppositories and creams for the treatment of internal and external vaginal yeast infections, respectively, as follows. Gallium citrate at 200 µM is combined with inactive ingredients including, in the case of a suppositories, gelatin, glycerin, lecithin, mineral oil, titanium oxide, and white petrolatum, or, in the case of external creams, benzoic acid, isopropylmyristate, polysorbate 60, potassium hydroxide, propyleneglycol, distilled water and stearyl alcohol. These formulations can be suitably packaged for use in a conventional manner.

Example 3 Disinfection of Inanimate Objects

A liquid formulation in a form of an aqueous solution of 5% by weight gallium phosphate and 5% by weight dimethyl benzyl ammonium chloride is prepared and packaged for use in households, hospitals, barber shops and beauty parlors as a surface treatment agent for disinfecting objects whose surfaces are prone to acting as sites for the growth of pathogenic organisms. Such a formulation can be used by application to such surfaces in a conventional manner.

Example 4 Animal Feeds

In the formulation of animal feeds whereby various nutrients and adjuvants are added to grains that are fed to domestic animals, gallium tartrate at 200 mg/kg feed is added to the feed separately or in combination with the aforesaid ingredients to ensure optimal mixing. The gallium tartrate can be applied as an aqueous solution using conventional equipment to achieve dispersal of the gallium tartrate throughout the feed.

EQUIVALENTS

Those skilled in the art to which the present invention is related will recognize, or be able to ascertain many equivalents to the specific embodiments of the invention described herein using no more than routine experimentation. Such equivalents are intended to be encompassed by the following claims.

All publications, patents and patent applications mentioned in this specification are herein incorporated by reference into the specification.

Citation or discussion of a reference herein shall not be construed as an admission that such is prior art to the present invention.

We claim:

1. A method for treating an infection of a drug resistant microorganism on a biological surface of a subject selected from the group consisting of a skin surface, eye surface, or vaginal surface,
   the method comprising: applying to the biological surface a therapeutically effective amount of a gallium compound selected from the group consisting of: gallium citrate, gallium phosphate, gallium chloride, gallium fluoride, gallium carbonate, gallium formate, gallium acetate, gallium sulfate, gallium tartrate, gallium oxalate, and gallium oxide,
   wherein the drug resistant microorganism is vancomycin-resistant *Enterococcus faecalis* (VRE),
   thereby controlling the growth of the microorganism.

2. The method of claim 1, wherein the gallium compound is formulated as a cream, lotion, solution, spray, aerosol, ointment, gel, or is formulated for slow diffusion.

3. The method of claim 1, wherein the subject is a human subject or a veterinary subject.

4. A method for disinfecting a biological surface of a drug-resistant species of a microorganism, the biological surface selected from the group consisting of a skin surface, a vaginal surface, and an eye surface, the method comprising:
   applying a therapeutically effective amount of a gallium compound selected from the group consisting of: gallium citrate, gallium phosphate, gallium chloride, gallium fluoride, gallium carbonate, gallium formate, gallium acetate, gallium sulfate, gallium tartrate, gallium oxalate, and gallium oxide, to the biological surface,
   wherein the drug resistant microorganism is vancomycin-resistant *Enterococcus faecalis* (VRE),
   thereby disinfecting the biological surface.

5. The method of claim 4, wherein the gallium compound is formulated as a cream, lotion, solution, spray, aerosol, ointment, gel, or is formulated for slow diffusion.

6. The method of claim 4, wherein the gallium compound is applied to the biological surface on or embedded in a bandage or wound dressing.

7. The method of claim 4, wherein the gallium compound is applied as soap, shampoo, or hand disinfectant.

* * * * *